United States Patent [19]

Ekstrom et al.

[11] 3,939,270
[45] Feb. 17, 1976

[54] PHARMACEUTICAL PREPARATIONS CONTAINING α-AMINOPENICILLINS

[75] Inventors: Bertil Ake Ekstrom; Berndt Olof Harald Sjoberg, both of Sodertalje, Sweden

[73] Assignee: Astra Lakemedel Aktiebolag, Sodertalje, Sweden

[22] Filed: Mar. 8, 1973

[21] Appl. No.: 339,364

Related U.S. Application Data

[62] Division of Ser. No. 178,426, Sept. 7, 1971, Pat. No. 3,873,521.

[30] Foreign Application Priority Data

Sept. 17, 1970 Sweden.............................. 12688/70
Nov. 20, 1970 Sweden.............................. 15720/70

[52] U.S. Cl. .............................................. 424/271
[51] Int. Cl.². ........................................ A61K 31/43
[58] Field of Search .................................... 424/271

[56] References Cited
UNITED STATES PATENTS 3,660,575  5/1972  Frederiksen et al................ 424/271
3,697,507  10/1972  Frederiksen et al................ 424/271

*Primary Examiner*—Jerome D. Goldberg
*Attorney, Agent, or Firm*—Brumbaugh, Graves, Donohue & Raymond

[57] ABSTRACT

New esters of α-aminopenicillins having the formula

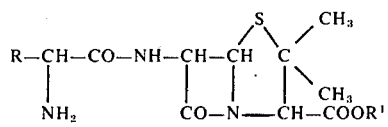

wherein R is $C_2$-$C_7$ alkyl;

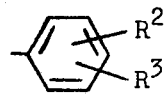

wherein $R^2$ = H or OH, $R^3$ = H or halogen;

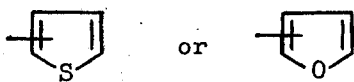

wherein $R^1$ is

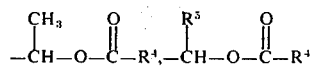

or $-CH_2NHCOO-R^4$ wherein $R^4$ = $C_1$-$C_4$ alkyl; $R^5$ = H, $CH_3$ or $C_2H_5$, useful as active ingredients of pharmaceutical preparation; processes for their preparation; chemical intermediates useful in said preparation; and methods for the treatment of infectious diseases.

19 Claims, No Drawings

PHARMACEUTICAL PREPARATIONS CONTAINING α-AMINOPENICILLINS

This is a division of application Ser. No. 178,426, filed Sept. 7, 1971, now U.S. Pat. No. 3,873,521.

The present invention relates to a process for the preparation of new esters of α-aminopenicillins having the formula

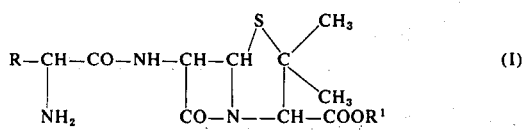

and pharmaceutical acceptable salts thereof in which formula R is selected from the group consisting of alkyl groups containing from 2 to 7 carbon atoms; the radical

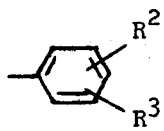

wherein $R^2$ is selected from the group consisting of hydrogen and hydroxy and $R^3$ is selected from the group consisting of hydrogen and halogen such as chlorine and fluorine; and the radicals

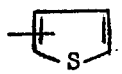

and

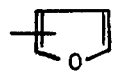

and wherein $R^1$ is selected from the group consisting of

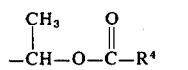

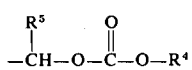

and

in which formulas $R^4$ is selected from the group consisting of alkyl groups containing from 1 to 4 carbon atoms; and $R^5$ is selected from the group consisting of H, —$CH_3$, and —$C_2H_5$.

Moreover, the invention refers to new intermediates for the preparation of the antibiotically active compounds according to the invention. These new intermediates, also useful as drugs, have the general formula

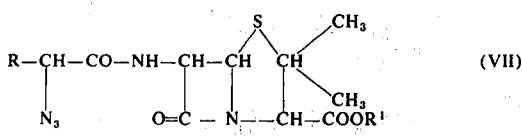

wherein R and $R^1$ have the above indicated meaning, or

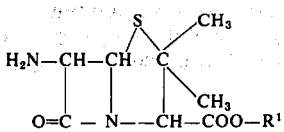

wherein $R^1$ has the above indicated meaning.

Salts of the new esters may be formed with inorganic acids, for instance hydrochloric acid, hydrobromic acid, hydroiodic acid or sulphuric acid, or with organic acids, for instance citric acid, tartaric acid or maleic acid. In view of the asymmetrical carbon atom in the side chain in the compounds having the formula I, said compounds exist in two epimeric forms, and the invention includes the preparation of both epimeric forms as well as mixtures thereof.

It is known that α-aminopenicillins are antibiotic substances having broad activity spectra. Among compounds particularly α-aminobezylpenicillin has gained a great importace, However, not only the antibacterial activity of a penicillin is of importance for its clinical effect, but also its pharmacological characteristics, such as oral absorption, tissue distribution, metabolism and rate of elimination. As regards α-aminobenzylpenicillin it has been found that said compound is orally absorbed relatively incompletely.

The compounds according to the invention are well absorbed orally and result in higher blood concentrations of the corresponding aminopenicillins than do the corresponding amounts of the latter as such. The esters are hydrolyzed somewhat in aqueous surroundings but considerably more when subjected to the influence of hydrolytic enzymes, for instance such present in blood serum and other human body fluids. This property of the esters is very important, since it results in a rapid release of the antibacterially active aminopenicillins from the esters when these are absorbed from the intestinal tract or is introduced in another manner into the flow of blood or into the tissue fluids.

Said compounds having the formula I are excellently tolerated and are preferably taken orally, either as such or in the form of their salts, and they can be intermixed with solid carriers or adjuvants or both. In such preparations the ratio between the therapeutic substance and the carriers and adjuvants may vary between 1 and 95 %. The preparations may either be processed to for instance tablets, pills or dragees or can be supplied to medical containers, such as capsules or as regards mixtures they can be filled on bottles. Pharmaceutically acceptable, organic or inorganic, solid or liquid carriers may be used, suitably for oral or enteral administration or for topical application, in manufacturing the preparations. Gelatine, lactose, starch, magnesium stearate, talc, vegetabilic and animalic fats and oils, vegetabilic rubber and polyalkylene glykol and other known carriers for pharmaceuticals are all suitable for manufacturing preparations of said compounds. The preferred salt of the esters is the hydrochloride, but salts with other inorganic or organic acids, also antibiotically active acids, may be used, for instance phosphates, acetates or salts with phenoxymethylpenicillin. Moreover the preparation may contain other pharmaceutical active components, being suitably administratable together with said esters when treating infectious disceases. For instance other suitable antibiotical substances.

In the treatment of bacterial infections in man, the compounds of invention are for example administered in amounts corresponding to 5 to 200 mg/kg/day, preferably in the range of 10 to 100 mg/kg/day in divided dosages, e.g. two, three or four times a day. They are administered in dosage units containing e.g. 175, 350, 500 and 1000 mg of the compounds.

Illustrative compounds according to the invention are:

$$R-CH-CO-NH-apa-COOR^1$$
$$|$$
$$NH_2$$

| R | R¹ | Name | Example | Method |
|---|---|---|---|---|
| $CH_3(CH_2)_5$ | $-CH(CH_3)-OCOOC_2H_5$ | 1'-ethoxycarbonyloxy-ethyl-α-amino-heptylphenicillanate | | |
| $CH_3$ | $-CH(CH_3)-OCOCH_3$ | 1'-acetoxy-ethyl-α-amino ethylpenicillinate | | |
| $(CH_3)_2CH-CH_2CH_2$ | $-CH(CH_3)-OCOCH_3$ | 1'-acetoxy-ethyl-α-amino-α-methylpentylpenicillinate | 5 | |
| $C_6H_5$ | $-CH(CH_3)-OCOCH_3$ | 1'-acetoxy-ethyl 6-(D-α-aminophenylacetamido)penicillanate | 7a, 6 | A |
| $C_6H_5$ | " | | 7c | B |
| $C_6H_5$ | " | | 7d | B |
| $C_6H_5$ | $-CH(CH_3)-OCOC_2H_5$ | 1'-propionyloxy-ethyl 6-(D-α-aminophenylacetamido)-penicillanate | 9 | A |
| $C_6H_5$ | $-CH(CH_3)-OCOCH(CH_3)_2$ | 1'-isobutyroxy-ethyl 6-(D-α-aminophenylacetamido)penicillanate | 10 | A |
| $C_6H_5$ | $-CH(CH_3)-OCOC_4H_9$ | 1'-valeryloxy-ethyl 6-(D-α-aminophenylacetamido)penicillanate | 10 | |
| $C_6H_5$ | $-CH_2OCOOCH_3$ | Methoxycarbonyloxymethyl 6-(D-α-aminophenylacetamido) penicillanate | 11, 8 | A |
| $C_6H_5$ | $-CH(CH_3)-OCOOC_2H_5$ | 1'-ethoxycarbonyl-ethyl 6-(D-α-aminophenylacetamido)penicillanate | 13, 14, 15 | A |
| $C_6H_5$ | " | | 16a | B |
| $C_6H_5$ | " | | 16b | B |
| $C_6H_5$ | $-CH(C_2H_5)-OCOOC_3H_7$ | 1'-propoxycarbonyloxy-propyl 6-D-α-aminophenylacetamido) penicillanate | | |
| $C_6H_5$ | $-CH(CH_3)-OCOOC_4H_9$ | 1'-butoxycarbonyloxy-ethyl 6-(D-α-aminophenylacetamido) penicillanate | | |
| $C_6H_5$ | $-CH_2OCOOC_2H_5$ | ethoxycarbonyloxymethyl 6-(D-α-aminophenylacetamido) penicillanate | 17 | A |
| $C_6H_5$ | $-CH_2OCOOC_3H_7$ | propoxycarbonyloxymethyl-6-(D-α-aminophenylacetamido) penicillanate | 18 | A |
| $C_6H_5$ | $-CH_2OCOOCH(CH_3)_2$ | isopropoxycarbonyloxymethyl 6-(D-α-aminophenylacetamido) penicillanate | 19 | A |

-continued

R—CH—CO—NH—apa—COOR$^1$
$\qquad$ |
$\qquad$ NH$_2$

| R | R$^1$ | Name | Example | Method |
|---|---|---|---|---|
| C$_6$H$_5$ | —CH$_2$—OCOOC$_4$H$_9$ | butoxycarbonyloxymethyl 6-(D-α-aminophenylacetamido)penicillinate | 20 | A |
| C$_6$H$_5$ | —CH$_2$—NHCOOC$_2$H$_5$ | ethoxycarbonylaminomethyl 6-(D-α-aminophenylacetamido) penicillanate | 21 8 | A |
| C$_6$H$_5$ | —CH$_2$NHCOOC$_4$H$_9$ | butoxycarbonylaminomethyl 6-(D-α-aminophenylacetamido) pencillanate | | |
| m-FC$_6$H$_4$ | —CH(CH$_3$)—OCOCH$_3$ | 1'-acetoxyethyl 6-(D-α-amino-m-fluorophenylacetamido)penicillanate | 22 | B |
| m-FC$_6$H$_4$ | —CH(CH$_3$)—OCOOC$_2$H$_5$ | 1'-ethoxycarbonyloxy-ethyl 6-(D-αamino-m-fluorophenyl-acetamido)penicillanate | 23 | A |
| m-FC$_6$H$_4$ | —CH$_2$OCOOC$_2$H$_5$ | ethoxycarbonyloxymethyl 6-(D-α-amino-m-fluorophenyl-acetamido)penicillanate | | |
| m-FC$_6$H$_4$ | —CH$_2$NHCOOC$_2$H$_5$ | ethoxycqrbonylaminomethyl 6-(D-α-amino-m-fluorophenyl acetamido)penicillanate | | |
| p-FC$_6$H$_4$ | —CH(CH$_3$)—OCOCH$_3$ | 1'-acetoxy-ethyl 6-(D-α-p-fluorophenylacetamido) penicillanate | 24 | A |
| p-FC$_6$H$_4$ | —CH(CH$_3$)—OCOOC$_2$H$_5$ | 1'-ethoxycarbonyloxy-ethyl 6-(D-α-amino-p-fluorophenyl-acetamido)penicillanate | 25 | A |
| p-ClC$_6$H$_4$ | —CH(CH$_3$)—OCOCH$_3$ | 1'-acetoxy-ethyl 6-(α-amino-p-chlorophenylacetamido) penicillanate | 26 | A |
| m-ClC$_6$H$_4$ | —CH(CH$_3$)—OCOOC$_2$H$_5$ | 1'-ethoxycqrbonyloxy-ethyl 6-(α-amino-m-chlorophenyl-acetamido)penicillanate | | |
| o-ClC$_6$H$_4$ | —CH$_2$OCOOCH$_3$ | methoxycarbonyloxymethyl 6-(α-amino-o-chlorophenyl-acetamido)penicillanate | | |
| p-OHC$_6$H$_4$ | —CH(CH$_3$)—OCOCH$_3$ | 1'-acetoxy-ethyl 6-(D-α-amino-p-hydroxyphenylacetamido) penicillanate | | |
| p-OHC$_6$H$_4$ | —CH(CH$_3$)—OCOOC$_2$H$_5$ | 1'-ethoxycarbonyloxy-ethyl 6-(D-α-amino-p-hydroxyphenyl-acetamido)penicillanate | 28 | B |
| m-OHC$_6$H$_4$ | —CH—OCOCH$_3$ | methoxycarbonyloxymethyl 6-(α-amino-m-hydroxyphenyl-acetamido)penicillanate | | |
| (3-thienyl) | —CH(CH$_3$)—OCOCH$_3$ | 1'-acetoxy-ethyl 6-(α-amino-3-thienylacetamido)penicillanate | 31 | B |

-continued

R—CH(NH₂)—CO—NH—apa—COOR¹

| R | R¹ | Name | Example | Method |
|---|---|---|---|---|
| " | —CH(CH₃)—OCOOC₂H₅ | 1'-ethoxycarbonyloxyethyl 6-(α-amino-3-thienylacetamido)penicillante | 30 | B |
|  (2-thienyl) | —CH(CH₃)—OCOOC₂H₅ | 1'-ethoxycarbonyloxy-ethyl 6-(α-amino-2-thienylacetamido)penicillanate | | |
|  (furyl) | —CH(CH₃)—OCOCH₃ | 1'-acetoxy-ethyl 6-(α-amino-3-furylacetamido)penicillanate | 29 | B |
|  (furyl) | —CH₂OCOOC₂H₅ | ethoxycarbonyloxymethyl 6-(α-amino-2-furylacetamido)penicillanate | | |
| 3-Cl-4-OHC₆H₃ | —CH(CH₃)—OCOOC₂H₅ | 1'-ethoxycarbonyloxy-ethyl 6-(α-amino-3-chloro-4-hydroxyphenyl-acetamido)penicillanate | | |
| m-FC₆H₄ | —CH₂NHCOOC₂H₅ | ethoxycarbonylaminomethyl 6-(D-α-amino-m-fluorophenylacet-amido)penicillanate | | |
| p-FC₆H₄ | —CH₂NHCOOCH₃ | methoxycarbonylaminomethyl 6-(D-α-amino-p-fluorophenyl-acetamido)penicillanate | | |
| o-ClC₆H₄ | —CH₂NHCOOC₂H₅ | ethoxycarbonylaminomethyl 6-(D-α-amino-o-chlorophenylacet-amido)penicillanate | | |
| C₆H₅ | —CH₂NHCOOC₄H₉ | butoxycarbonylaminomethyl 6-(D-α-aminopehnylacetamido)penicillanate | | |
| | | Absorption formulations | 32 | |
| | | Hydrolysis formulations | 33 | |
| | | Pharmaceutical formulations | 34 | |

The preparation of compounds of formula I according to the invention is made either by a) reacting a α-substituted penicillin or salt thereof of the formula II

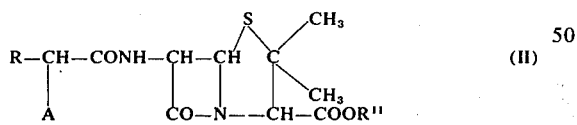   (II)

wherein A is an amino group, a substituted amino group or a group that can be transformed or converted to an amino group, and R¹¹ is hydrogen or a cation, with a compound having the formula III

XR¹   (III)

wherein X indicates a halogen atom or a functionally equivalent group such as an alkylsulphonyloxy or an arylsulphonyloxy group, and R is the same as previously indicated, for the formation of compounds having formula I if A is an amino group, or if A is a substituted amino group or a group that can be converted to an amino group for formation of a compound having formula IV

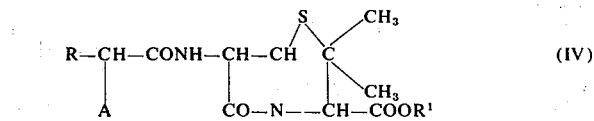   (IV)

wherein R, A and R¹ have the meaning indicated above, the A-substituent of that intermediate being then converted to an amino group, or b. reacting a compound having the formula

R—CH(A)—CO—Y¹   (V)

with an ester of 6-amino penicillanic acid or a derivative thereof according to the reaction sequence

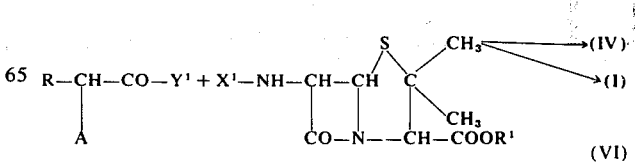

in which formulae R, A and $R^1$ have the meaning indicated above, and the radicals CO—$Y^1$ and $X^1$—NH— are such radicals, that can react with each other under formation of a —CO—NH—linkage for the formation of compounds having the formula I, if A is an amino group, or compounds having the formula IV if A is thereafter converted to an amino group.

In the embodiment (a) the reaction takes place according to the following reaction sequence

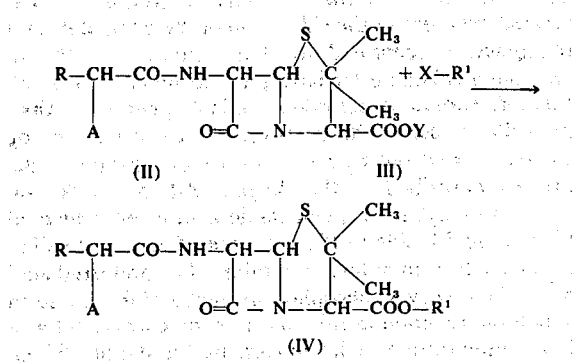

In the formulas of the sequence R and $R^1$ have the meaning as previously indicated. A is an amino group or a substituted amino group Z—NH— or a group that can be transformed or converted to an amino group, for instance an azido or nitro group or a halogen atom, such as chlorine and bromine, —COOY and X—$R^1$— represent groups that are able to react with each other under the formation of the grouping —COO—$R^1$. As an example, Y may be hydrogen or an alkali metal atom or a tertiary ammonium group and X may be a halogen atom, preferably chlorine or bromine, or a group functionally equivalent therewith, alkylsulphonyloxy or arylsulphonyloxy radical. The compounds formed by the reaction are esters of α-A-substituted penicillins (IV). If A is the group $NH_2$ the formula IV represents the compounds of the invention, whereas, when A has other meanings, the formula indicates interesting intermediates in the synthesis of the compounds of the invention.

A comprehension of characteristica of substituent A is that it is selected among groups, that after the above mentioned reaction can be converted to an amino group with methods that are sufficiently mild to avoid destruction of the molecule at the ester group or at the lactame ring. Especially all such groups A that have been used when synthetizing aminopenicillins are useful. Thus, the substituent A preferably has the formula Z—NH—, wherein Z is a benzyloxycarbonyl group, a parahalogen, paranitro or paramethoxybensyloxycarbonyl group, a β,β,β-trichloroethyloxycarbonyl group or Z may be a sulphur-containing radical, for instance a trithylsulphenyl group, or an arylsulphonyl group, for instance an orthonitrophenylsulphenyl group. Z may also be tripehnylmethyl (also called trityl) or a group obtained by reacting the free amino group with a β-dicarbonyl compound, such as acetylacetone, an acetic ester or benzoyl acetone for formation of enamines or Schiffs bases. Generally it may be said, any Z-group that can be removed by reduction, weak acid hydrolysis or by other mild reactions known per se, will be suitable. The starting materials for formula II, wherein A is different from $NH_2$, are known as intermediates in the synthesises of α-aminobenzylpenicillins. They exist in two epimeric forms. If the starting materials are prepared in the form of the D- or L-epimer, the corresponding epimeric form of the compounds of the invention is obtained. If, on the other hand, a mixture of the epimeric forms of starting materials is used, a mixture is obtained. If desired this mixture can be separated in the two isomers, for instance by fractional chrystallisation. The methods for the preparation of starting materials having the formula II are standard methods used within the peptide chemistry and include for instance conversion of phenyl acetic acid to A-substituted phenyl acetic acid, where A has the meaning indicated above, followed by a reaction between a reactive derivative of said intermediate and 6-aminopenicillanic acid, wherein the amino group may be free or substituted, for instance with a trimethylsilyl radical. Some of the starting materials having formula II may also be prepared from α-aminobenzylpenicillin or salts thereof.

The reaction of compounds having the formula II with compounds having formula III may be carried out at or below room temperature or by careful heating to the boiling point of the solvent used, depending on the meaning of Y and X. It is possible to use different organic solvents or mixtures thereof with water, for instance acetone, dioxane, tetrahydrofurane, methylchloride or dimethylformamide. The reaction products are chrystalline or oily products, that may be used in the next step without further purification. By repeated precipitation the oily products may be converted to chrystalline or amorphous powders.

The subsequent reaction step (IV, I), wherein the A-group is transformed or converted to an amino group, can depending on the meaning of A be carried out by different methods known from peptide synthesis and aminopenicillin synthesis.

Catalytic hydrogenation is preferred if A has the formula Z—NH—, and Z means benzyloxycarbonyl or closely related derivatives thereof, or if Z is trityl. The hydrogenation is preferably carried out at room temperature and either at atmospheric or slightly elevated pressure in a solvent that may be a non-reducing organic solvent or a mixture of such solvent with water. The preferred catalysts are noble metal catalysts, for instance palladium or platinum catalysts or Raney-nickel, but also other catalysts can be used. Electrolytic reduction can also be used in these cases. If Z is a β,β,β-trichloroethyloxycarbonyl group, reduction with Zn in acetic acid is preferred. A weak acid hydrolyse is preferred, if Z is a sulphur-containing radical, an enamine or a Schiffs base, for instance a hydrolyse at a pH-value of about 2 in a dilute solution of hydrogen chloride in aqueous acetone. It is also known in the literature to remove an o-nitrophenylsulphenyl-radical by a nucleophilic attack on the sulphur atom of the sulphenamide group, and in this case best yield is obtained with potassium or sodium iodide, sodium thiosulphate, sodium hydrosulfide, sodium hydrosulphite or potassium thiocyanate. Alternatively, the sulphenamide compound may be reacted with a thiophenol in an organic solvent, e.g. dimethylformamide. Other sulphenamide radicals are removed in the same way. If A is an azido or nitro group such groups may be converted to the free amino group in a manner known per se when the azido and nitro group is catalytically hydrogenated with a noble metal catalyst or with Raney-nickel or by electrolytic reduction. If A is a halogen atom, for instance bromine, it is converted to an amino group by amination, for instance with hexamethylentetramine.

In the embodiment b) a compound having formula V

 (V)

is reacted in a manner known per se with an ester of 6-amino penicillanic acid having formula VI

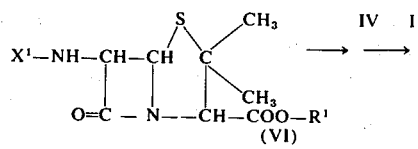

In these formulae R and A have the same meaning as above, and radicals —CO — $Y^1$ and $X^1$ —HN— are of such a nature as to be able to react with each other under formation of a group —CONH—. For instance —CO—$Y^1$ can be the radical of an acid halide, for instance an acid cloride or acid bromide, an anhydride, a mixed anhydride with an alkylcarbonic acid, for instance isobutyl carbonic acid, a carbonic acid, an inorganic acid or a sulphonic acid, or may be a radical obtained by reacting the α-substituted phenylacetic acid and a carbodiimide or N,N'-carbonyldiimidazol or an other compound reacting in a similar way. $X^1$ may be hydrogen or a trialkylsilyl group, wherein the alkyl group has not more than 5 carbon atoms. The reaction can be carried out in an organic solvent or a mixture of such solvent with water, either at low temperature or at slightly elevated temperature. Suitable solvents are methylene chloride, chloroform, ethylacetate, acetone, dimethyl formamide or diethylacetamide, ether, tetrahydrofurane, dioxane or similar inert solvents. The reaction products are isolated in a conventional manner, for instance by repeated precipitation or by removal of the solvent, followed by recrystallisation from a solvent. Compounds having formula V are known compounds that can be produced by standard methods known in peptide chemistry.

The compounds having the formula VI are new compounds that are intermediates in the synthesis of compounds having formula I. They may be prepared by reacting 6-aminopenicillanic acid in the form of a salt, for instance an alkali metal salt or a triethyl ammonium salt with a halogen alkylester having formula X—$R^1$ (III), wherein X is a halogen atom, preferably a chlorine or bromine atom, or a functionally equivalent group such as a sulphonyloxyradical. The 6-aminopenicillanic acid can be used as such, or the 6-amino group may be protected during the esterifying process. Only protecting groups that may be easily removed without causing weakening of the lactame ring or the ester group are suitable in this case, for instance triphenylmethyl or trimethylsilyl radicals. The reaction is carried out in an inert organic solvent, for instance acetone, dimethylformamide or methylene chloride, and at or below room temperature or somewhat elevated temperature. If the amino group is protected the removal of the protecting group can be carried out in different ways, for instance by hydrogenolyse or hydrolyse under neutral or acid conditions, by which the lactame ring and the ester group are not attacked. Reaction products having the formula VI ($X^1$ = H) are suitably isolated in the form of their acid addition salts with for instance p-toluene sulphonic acid or other inorganic or organic acids, such as sulphuric acid, phosphoric acid, hydrochloric acid, acetic acid, maleic acid, tartaric acid and other similar acids.

The compounds of formula VI may also be prepared by esterifying the industrially available penicillins or preferably their salts with a compound having the above formula III under similar conditions as described, whereafter the side chain of the penicillin ester obtained is separated for the formation of the α-aminopenicillanic ester having the formula VI or a salt thereof. Preferably benzylpenicillin or phenoxymethylpenicillin is used. The cleavage of the amide binding can be carried out by means of a modification of the process described in the Belgian Pat. No. 698,596, wherein 6-acylamino penicillanic acid ester is reacted with an acid halide in the presence of an acid-binding agent, such as quinoline or pyridine. The preferred acid halide is, however, phosphorous pentachloride, due to which the reaction in this case may be carried out at a low temperature, which will increase the stability of the intermediate formed, probably being an imino halide. The reaction can be carried out in different solvents, but the preferred solvents are chloroform and methylene chloride.

The intermediate is not isolated, but treated with a primary alcohol in excess for formation of an iminoether. The reaction temperature and reaction time depend on the alcohol used. In most cases temperatures between —20°C and +20°C are suitable.

Neither is the iminoether isolated, but subjected to an acid alcoholysis or hydrolysis, causing cleavage of the binding C-N and the corresponding 6-aminopenicillanic acidester having formula VI is formed. Alternatively, the side chain may be enzymatically cleaved in a manner known per se, e.g. such as disclosed in French Pat. specification No. 1,576,027. In the methods generally used, the esters of 6-aminopenicillanic acid can be isolated from the reaction mixture as such or in the form of salts with inorganic or organic acids, for instance in the form of hydrochloride or tosylate.

Preferred compounds of the invention are:
1'-Acetoxyethyl 6-(D-α-aminophenylacetamido)-penicillanate
1'-Ethoxycarbonyloxyethyl 6-(D-α-aminophenylacetamido)penicillanate
Ethoxycarbonyloxymethyl 6-(D-α-aminophenylacetamido)penicillanate
1'-acetoxyethyl 6-(D-α-amino-p-hydroxyphenylacetamido)penicillanate
1'-Ethoxycarbonyloxyethyl 6-(D-α-amino-p-hydroxyphenylacetamido)penicillanate
Ethoxycarbonyloxymethyl 6-(D-α-amino-p-hydroxyphenylacetamido)penicillanate
1'-Acetoxyethyl 6-(D-α-amino-m-fluorophenylacetamido)penicillanate
1'-Ethoxycarbonyloxyethyl 6-(D-α-amino-m-fluorophenylacetamido)penicillanate
Ethoxycarbonyloxymethyl 6-(D-α-amino-m-fluorophenylacetamido)penicillanate
1'-acetoxyethyl 6-(D-α-amino-p-fluorophenylacetamido)penicillanate
1'-Ethoxycarbonyloxyethyl 6-(D-α-amino-p-fluorophenylacetamido)penicillanate Ethoxycarbonyloxymethyl 6-(D-α-amino-p-fluorophenylacetamido)penicillanate
1'-Acetoxyethyl 6-(D-α-amino-3-thienylacetamido)-penicillanate
1'-Ethoxycarbonyloxyethyl 6-(D-α-amino-3-thienylacetamido)penicillanate
Ethoxycarbonyloxymethyl 6-(D-α-amino-3-thienylacetamido)penicillanate
1'-acetoxyethyl 6-(D-α-amino-3-furylacetamido)-penicillanate
1'-Ethoxycarbonyloxymethyl 6-(D-α-amino-3-furylacetamido)penicillanate
Ethoxycarbonyloxymethyl 6-(D-α-amino-3-furylacetamido)penicillanate.

The processes of the invention are illustrated by the following Examples:

EXAMPLE 1

1'-Acetoxyethyl benzylpenicillinate.

α-Chloroethyl acetate (312 g, 2.54 mole) was added dropwise to a stirred solution of potassium benzylpenicillinate (316 g, 0.85 mole) in 70 % dioxane (1275 ml) at room temperature while the mixture was kept at pH 8 by addition of sodium bicarbonate. After the addition of the chloro ester was complete, sodium bicarbonate was added so that the total amount of it was 413 g (5.1 mole). The reaction mixture was stirred for 48 hours and then extracted repeatedly with ethyl acetate. The combined extracts were washed with water and brine, dried and evaporated in vacuo at 30°C. The oily residue was triturated five times with toluene which was distilled off in vacuo at 70°C to give the 1'-acetoxyethyl benzylpenicillinate (144 g) as an oil which solidified on standing. A part of it was crystallized from a mixture of methanol-ether-petrolether to give the analytically pure compound m.p. 128°–130°C (Found: C 57.28; H 5.77; N 6.58; O 23.05; S 7.82 %. Calculated for $C_{20}H_{24}N_2O_6S$ : C 57.13 %, H 5.75 %, N 6.66 %, O 22.83 % and S 7.63 %). The product showed strong IR-absorption at 1785-1750 $cm^{-1}$ indicating the presence of β-lactam rings and ester groups.

EXAMPLE 2

1'-Acetoxy-ethyl 6-aminopenicillanate hydrochloride.

Dry quinoline (11.6 g, 0.09 mole) was added at room temperature dropwise to a stirred mixture of phosphorous pentachloride (11.7 g, 0.056 mole) and dry methylene chloride (110 ml). After stirring for 15 min the reaction mixture was chilled to −20°C and with continued stirring treated dropwise with 1'-acetoxyethyl benzylpenicillinate (20.8 g, 0.05 mole) dissolved in dry methylene chloride (30 ml). 15 min after the addition was complete the mixture was chilled to −30°C and 1-propanol (37 ml) was rapidly added so that the temperature did not rise above −15°C. The mixture was stirred for a further 30 min at −30°C when ice-cooled brine (20 %, 75 ml) was added with vigorous stirring. After stirring for 10 min at −10°C petrol ether (155 ml) was added, followed by a second portion (175 ml) after a further 10 min, yielding a crystalline precipitate which was collected by filtration, washed with brine (70 ml) and dried to give the hydrochloride of 1'-acetoxyethyl 6-aminopenicillanate (14.2 g). The product showed strong IR absorption at 1780 – 1725 $cm^{-1}$ showing the presence of β-lactam and ester carbonyls.

An analytical sample, m.p. 160°C, was obtained by recrystallisation of the product from ethanol-ether.

(Found: C 44:1, H 5.67, N 7.56, Calculated for $C_{12}H_{19}ClN_2O_5S$ : 42.53 %, H 5.37 %, N 8.29 %.

EXAMPLE 3

1'-Ethoxycarbonyloxyethyl benzylpenicillanate.

Potassium benzylpenicillinate (242 g, 0.65 mole), α-chlorodiethyl carbonate (297 g, 1.95 mole) and sodium bicarbonate (327.5 g, 3.90 mole) in 70 % dioxane (1600 ml) were stirred for 66 hours at room temperature. The solid phase was removed by filtration and washed with dioxane. The combined filtrates were concentrated in vacuo and taken up into a mixture of benzene (2 liter) and saturated sodium bicarbonate solution (1 liter). The organic phase was washed with brine, dried and evaporated in vacuo to give 1'-ethoxycarbonyloxyethyl benzylpenicillinate (96.1 g) as a thick oil which solidified on standing. An analytical sample, m.p. 108°–109°C, was obtained by recrystallisation from acetone - petrol ether.

(Found: C 55.98, H 5.66, N 6.29, O 24.34, S 7.20 %. Calculated for $C_{21}H_{26}N_2O_7S$: C 56.10, H 5.83, N 6.23, O 24.88, S 7.13 %.)

The product showed strong IR absorption at 1780 – 1750 $cm^{-1}$ due to the β-lactam and ester carbonyls.

EXAMPLE 4

1'-Ethoxycarbonyloxyethyl 6-aminopenicillinate.

The hydrochloride of 1'ethoxycarbonyloxyethyl 6-aminopenicillanate was prepared from 1'-ethoxycarbonyloxyethyl benzylpenicillinate (62.8 g, 0.14 mole) according to the procedure described in Example 2. The product (28.8 g) was obtained as a glassy residue showing strong IR-absorption at 1765 $cm^{-1}$, showing the presence of β-lactam and ester carbonyls.

EXAMPLE 5

1'-Acetoxyethyl α-amino-δ-methylpentylpenicillinate

Potassium α-azido-δ-methylpentylpenicillinate (2.9 g, 0.0071 mole) in 70 % dioxane was stirred for 2 days with α-chloroethyl acetate (2.6 g, 0.021 mole) in the presence of sodium bicarbonate (3.6 g, 0.043 mole). The reaction mixture was diluted with water and extracted with ethyl acetate. The combined organic extracts were washed with water, dried and evaporated in vacuo to give 1'-acetoxyethyl α-azido-δ-methylpentylpenicillinate (1.3 g) as an oily residue.

The product showed strong absorption at 2120 $cm^{-1}$ and 1750 $cm^{-1}$ characteristic of the azido group and the β-lactam and ester moeties respectively. It was dissolved in 70 % ethanol and hydrogenated for 30 min over a pre-hydrogenated Raney-nickel catalyst. The catalyst was removed by filtration and washed with ethanol. The filtrate was diluted with water and extracted with ethyl acetate. The combined organic extracts were washed with water and then extracted with water with addition of dilute hydrochloric acid until the pH reached 2.5. The aqueous phase was separated and lyophilized to give the hydrochloride of 1'-acetoxyethyl α-amino-δ-methylpentyl penicillinate (0.7 g) as slightly yellow crystals.

The product showed strong β-lactam absorption at 1770 – 1740 $cm^{-1}$ and inhibited the growth of Staph. aureus Oxford at 0.63 μg/ml.

EXAMPLE 6

1'-acetoxyethylester of 6-(D-α-azidophenylacetamido)-penicillanic acid.

The sodium salt of 6-(D-α-azidophenylacetamido)-penicillanic acid (96%, 12.4 g, 0.03 mole) was dispersed in dry dimethylformamide (30 ml) and under stirring and icecooling with α-chloroethylacetate (3.7 g, 0.03 mole) dissolved in dry dimethylormamide (15 ml) was added. After 30 minutes the stirring was continued without cooling over the night. The reaction mixture was poured into a saturated sodium bicarbonate solution (500 ml), a white emulsion being obtained. This emulsion was diluted with $H_2O$ (400 ml) and extracted with ether 3 times. The combined either phases were washed with $H_2O$ and saturated sodium chloride solution and dried. The evaporisation in vacuo of the ether solution gave the α-acetoxyethylester of 6-(D-α-azidophenylacetamido)-penicillanic acid (3.1 g) having a purity of 58 % (hydroxylamine essay).

The product had a strong IR-absorption at 2100 cm$^{-1}$ and 1760 cm$^{-1}$ showing the presence of an azido group and a β-lactame ring.

EXAMPLE 7

1'-Acetoxyethyl 6-(D-α-aminophenylacetamido)penicillanate a. α-acetoxyethyl 6-(D-α-azidophenylacetamido)-penicillanate (58 %, 2.8 g), dissolved in ethyl acetate (40 ml) was treated with 0.2 M $NaH_2PO_4$ (40 ml), acidified to pH 2.2 with 2 M hydrochloric acid and hydrogenated over a palladium on carbon catalyst at ambient conditions for 2 hours. The caralyst was removed by filtration and washed with ethyl acetate and buffer. The organic phase of the combined filtrates was separated and extracted with water at pH 2.1. The combined acidic aqueous phases were washed with ether, layered with ethyl acetate and neutralized by addition of 2 N sodium hydroxide while stirring. The aqueous phase was separated and extracted once with ethyl acetate. The combined ethyl acetate extracts of the neutralized aqueous solution were washed with brine and water and extracted twice with water at pH 2.5 by addition of 2 M hydrochloric acid. The combined acidic aqueous extracts were washed with ether and concentrated in vacuo at 25°C to give an oily residue, which was dissolved in isopropanol and evaporated in vacuo repeatedly to give the hydrochloride of 1'-acetoxyethyl 6-(D-α-aminophenylacetamido)pencillanate (1.1 g) as a slightly coloured powder with a purity of 100 % (hydroxylamine essay).

The product inhibited the growth of Staph. aureus Oxford at a concentration of 0.32 μg/ml, of E. coli and P. mirabilis at 50 μg/ml.

b. 1'-Acetoxyethyl 6-(D-α-azidophenylacetamido)-penicillanate [strong IR-absorption at 2100 cm$^{-1}$ (azido group) and 1780 – 1760 cm$^{-1}$ (β-lactam, ester)] was prepared according to the method of Example 1 from sodium 6-(D-α-azidophenylacetamido)penicillanate (397 g, 1 mole), α-chloroethyl acetate (368 g, 3 mole) and sodium bicarbonate (504 g, 6 mole). The azido ester in ethyl acetate (800 ml) was hydrogenated at ambient conditions over a palladium (5 %) on carbon catalyst (25 g). The catalyst was removed by filtration and washed with ethyl acetate. The combined filtrates were extracted with water at pH 2.5 by addition of dilute hydrochloric acid. Lyophilization of the aqueous phase gave the hydrochloride of 1'-acetoxyethyl 6-(D-α-aminophenylacetamido)penicillanate (110 g), m.p. 160°–164°c,l (decomp.) $[\alpha]_D^{20}$ + 184°C (C = 1, $CHCl_3$); + 179.9 (1 = 1, 50 % isopropanol).

(Found: C 50.78, H 5.49, N 8.76, O 20.22, S 6.58, Cl 7.39 %. Calculated for $C_{20}H_{25}N_3O_6SCl$: C 50.90, H 5.55, N 8.90, O 20.34, S 6.79, Cl 7.51 %.)

The product showed strong IR-absorption at 1780 – 1755 cm$^{-1}$, showing the presence of β-lactam and ester carbonyls and was found to inhibit the growth of Staph. aureus Oxford at a concentration of 0.25 μg/ml.

c. A suspension of dicyclohexylammonium α-(o-nitrophenylsulphenyl)aminophenylacetate (4.9 g, 0.01 mole) and the hydrochloride of 1'-acetoxyethyl 6-aminopenicillanate (3,4 g, 0.01 mole) in chloroform (60 ml) was stirred over night. Dicyclohexyl carbodiimide (2.2 g, 0.01 mole) was added and stirring was continued for 6 hours. The reaction mixture was filtered and washed with water, dilute sulphuric acid, N potassium bicarbonate and water, dried and evaporated to dryness in vacuo. The yellow residue was treated with ethyl acetate, filtered and evaporated again to give a residue which was crystallized from ethyl acetate/petroleum ether to give 1'-acetoxyethyl 6-[D-α-(o-nitrophenylsulphenyl)amino-phenylacetamido]penicillanate (1.5 g), m.p. 122°–5°C.

The product had a strong IR absorption 1780 – 1750 cm$^{-1}$ showing the presence of β-lactam and ester carbonyls.

The o-nitrophenylsulphurylamino ester (1.2 g, 0.002 mole) was dissolved in 75 % dioxane (17 ml) and adjusted to pH 3 by addition of 2 N hydrochloric acid. Sodium iodide (1.2 g, 0.008 mole) was added and the mixture was stirred and kept at pH 3 by addition of acid. After 20 minutes the iodine formed was reduced with 2 N sodium thiosulphate and the mixture was neutralized and extracted with ethyl acetate after addition of water. The combined organic extracts were washed with water and extracted into water by addition of 2 N hydrochloric acid to the stirred mixture until the pH reached 2. The aqueous phase was washed with ethyl acetate and lyophilized to give the hydrochloride of 1'-acetoxyethyl 6-(D-α-aminophenylacetamido)-penicillanate (0.15 g). The product was identified with the one prepared in Example 7a with the aid of its IR spectrum.

The intermediate 1'-acetoxyethyl 6-[D-α-(o-nitrophenylsulphuryl)aminophenylacetamido]penicillanate was also obtained by acylating 1'-acetoxyethyl 6-aminopenicillanate with the mixed ethoxyformic anhydride of 2-(o-nitrophenylsulphenyl)aminophenylacetic acid or by reacting 6-[D-α-(o-nitrophenylsulphenyl)aminophenylacetamido]penicillanic acid with α-chloroethyl acetate.

EXAMPLE 8

By repeating the procedure of Example 7a the following esters of 6-(D-α-aminophenylacetamido)-penicillanic acid hydrochloride were obtained from the corresponding azido compounds.

| Ester | Content (%) | MIC (μg/ml) Staph.aur. Oxford | E.coli | P.mirabilis |
|---|---|---|---|---|
| Methoxycarbonyloxy-methylester | 69 | 0.16 | 25 | 6.25 |
| Ethylcarbamato-methylester | 48 | 0.16 | 12.5 | 6.25 |

(termination of concentration according to the hydroxamate method; antibacterial activity determined by tube dilution procedure in broth).

All esters of Examples 7 and 8 were hydrolyzed under the formation of 6-(D-α-aminophenylacetamido)penicillanic acid by incubation ("°C) with human serum.

EXAMPLE 9

1'-Propionyloxyethyl 6-(D-α-aminophenylacetamido) penicillanate.

Sodium 6-(D-α-azidophenylacetamido)penicillanate (6.0 g, 0.015 mole), α-chloroethyl pripionate (5.7 g, 0.042 mole) and sodium bicarbonate (7.1 g, 0.084 mole) were stirred at room temperature for 65 hours in 70 % dioxane (100 ml). The solid phase of the reaction mixture was removed by filtration and washed with dioxane. The combined filtrates were concentrated in vacuo and treated with a mixture of benzene (50 ml) and saturated sodium bicarbonate solution (25 ml). The organic phase was separated, washed with brine, dried and evaporated in vacuo to give 1'-propionyloxyethyl 6-(D-α-azidophenylacetamido)penicillanate (1.3 g) as a yellow oil, characterized by strong IR absorption at 2110 and 1780 – 1750 $cm^{-1}$, showing the presence of azido, β-lactam and ester moieties.

The azido ester in ethyl acetate (50 ml) was hydrogenated for 30 minutes at ambient conditions over a prehydrogenated palladium (5 %) on carbon catalyst (1.3 g). The catalyst was removed by filtration and washed with ethyl acetate and water. The pH of the combined filtrates was adjusted to 2.2 by addition of dilute hydrochloric acid. The aqueous phase was separated and the organic phase was extracted once more with water at pH 2.2. The combined aqueous extracts were lyophilized, to give the hydrochloride of 1'-propionyloxyethyl 6-(D-α-aminophenylacetamido) penicillanate (0.6 g) as an amorphous solid.

The product showed in its IR spectrum strong β-lactam and ester carbonyls absorption at 1760 $cm^{-1}$. It was found to inhibit the growth of *Staph. Aureus* Oxford at a concentration of 0.63 μg/ml.

EXAMPLE 10

1'-Isobutyroxyethyl and 1'-valeryloxyethyl 6-(D-α-aminophenylacetamido)penicillanates.

Repeating the experiments described in Example 17 but replacing α-chloroethyl propionate with α-chloroethyl isobutyrate and α-chloroethyl valerate gave the intermediate 1'-isobutyroxyethyl and 1'-valeryloxyethyl 6-(D-α-azidophenylacetamido)penicillanates, respectively.

The compounds were characterized by their IR spectra containing strong absorption bands at 2100 $cm^{-1}$ and 1780 – 1730 $cm^{-1}$ attributable to the azido, β-lactam and ester moieties. On hydrogenation they gave 1'-isobutyroxyethyl and 1'-valeryloxyethyl 6-(D-α-aminophenylacetamido)penicillanates, respectively, isolated as hydrochlorides. The amino esters had strong β-lactam and ester absorption in their IR spectra around 1760 $cm^{-1}$.

EXAMPLE 11

Methoxycarbonyloxymethylester of 6-(D-α-azidophenylacetamido)penicillanic acid.

By replacing the α-chloroethylacetate by monochloro-dimethylcarbonate (3.7 g, 0.03 mole) in Example 6, but otherwise operating in the same way as in said Example the methoxycarbonyloxymethylester of 6-(D-α-azidophenylacetamido)-penicillanic acid (6.6 g) having a content of 76.5 % (hydroxylamine essay) was obtained.

The product showed IR-absorption at 2100 $cm^{-1}$ ($N_3$-group) and 1765 $cm^{-1}$ (β-lactame ring).

EXAMPLE 12

Methoxycarbonyloxymethyl 6-(D-α-aminophenylacetamido) penicillanate.

According to the method of Examples 11 and 8, methoxycarbonyloxymethyl 6-(D-α-aminophenylacetamido)penicillanate was prepared, starting from sodium 6-(D-α-azidophenylacetamido) penicillanate (24.2 g, 0.06 mole), chloromethyl methylcarbonate (6.2 g, 0.06 mole). The compound was isolated as its hydrochloride (5.6 g) m.p. 145°–150°C (decomp.) $[\alpha]_D^{20}$: +182.5 (C = 1, $CHCl_3$); + 191.2 (C = 1, 50 % isopropanol), (Found: C 48.04, H 5.27, O 23.67, N 8.94, S 6.57, and Cl 7.36 %. Calculated for $C_{19}H_{24}N_3O_7S$ Cl : C 48.15, H 5.10. N 8.87, O 23.63, S 6.77 and Cl 7.48 %).

The product showed strong IR absorption at 1780 – 1760 $cm^{-1}$ showing the presence of β-lactam and ester carbonyls. It was found to inhibit the growth of *Staph. Aureus* Oxford at a concentration of 0.13 μg/ml

EXAMPLE 13

1'ethoxycarbonyloxy-ethyl 6-(D-α-azido-phenylacetamido)pencillanate.

The sodium salt of 6-(D-α-azidophenylacetamido)-penicillanic acid (4.0 g 0.01 mole) was dispersed in dry dimethyl formamide (10 ml) and treated under stirring at 50°C with α-chloro-diethyl carbonate (1.5 g 0.01 mole) dissolved in dry dimethyl formamide (6 ml). After stirring for 20 hours at 50°C the reaction mixture was cooled and poured into an icecold, saturated sodium bicarbonate solution and extracted three times with ether. The combined ether phases were washed with water and brine and dried. Evaporation in vacuum gave the α-ethyoxycarbonyloxi ethylester of 6-(D-α-azidophenylacetamido)-penicillanic acid (2.6 g) in the form of a yellow-brown glass.

The product had strong IR-absorption at 2100 $cm^{-1}$ and 1750 $cm^{-1}$ showing the presence of an azido group and β-lactame ring and an ester group.

EXAMPLE 14

1'-ethoxycarbonyloxy-ethyl 6-(D-α-aminophenylacetamido) penicillanate.

The α-ethoxycarbonyloxy ethylester of 6-(D-α-azidophenylacetamido-penicillanic acid (2.5 g) was dissolved in ethyl acetate (40 ml) and 0.4 mole $NaH_2PO_4$ acidified to pH 2.2 with 2 mole hydrochloric acid (40 ml) and 10 % palladium on carbon catalyst (4 g) was added and hydrogenation was carried out at normal pressure for 0.5 hour. The catalyst was separated by filtration and washed with ethyl acetate and buffer solution. The filtrate was separated and the organic phase was extracted with water at pH 2.1. The combined acid water phases were washed with ether, ethyl acetate was added and neutralisation was carried out under stirring with 2 mole NaOH. The phases were separated and the water solution was reextracted with ethyl acetate. The two ethyl acetate extracts were combined, washed with brine and water and extracted with water at pH 2.5 by the addition of 2 mole hydrochloric acid. The extraction of the ethylacetate phase was repeated once. The combined acid water extracts were washed with ether and concentrated in vacuo at 25°C. The semi-solid residue was dissolved in isopropanole and reconcentrated, the procedure being repeated once. The residue was stirred with ether, filtrated and washed with ether, giving the α-ethoxycarbonyloxy ethylester of 6-(D-α-aminophenyl acetamido) penicilanic acid hydrochloride (0.8 g) as a yellow-white powder having a content of 86.4 % (hydroxylamine essay).

The product inhibited the growth of Staph. Aureus Oxford at a concentration of 0.13 μg/ml and of E.coliat 125 μg/ml (solution test on agar) and contained in its IR-spectrum a strong absorption band at 1750 cm$^{-1}$ showing presence of a β-lactame and an ester function.

The azido ester (3.2 g) was also obtained by treating the hydrochloride of 1′-ethoxycarbonyloxyethyl 6-aminopenicillanate (3.3 g, 0.01 mole) in dry dimethylformamide (50 ml) with α-azidophenylacetyl chloride (2 g, 0.01 mole) in presence of triethylamine (2 g, 0.01 mole). After dilution of the reaction mixture with water the ester was isolated by extraction with ethyl acetate.

EXAMPLE 15

1′-Ethoxycarbonyloxyethyl 6-(D-α-aminophenylacetamido) penicillanate:

According to the method of Example 1 1′-ethoxycarbonyloxyethyl 6-(D-α-azidophenylacetamido)penicillanate (98 g) was prepared from sodium 6-(D-α-azidophenylacetamido)penicillanate (397 g, 1 mole), α-chlorodiethylcarbonate (458 g, 3 mole) and sodium bicarbonate (504 g, 6 mole), The product showed strong IR absorption at 2090 cm$^{-1}$ and 1780 – 1750 cm$^{-1}$ showing the presence of azido group and β-lactam and ester carbonyls.

It was dissolved in ethyl acetate (700 ml) and hydrogenated at ambient conditions over a palladium (5 %) on carbon catalyst (18 g). The catalyst was removed by filtration and washed with ethyl acetate. The combined filtrates were extracted with water at pH 2.5 by addition of dilute hydrochloric acid. Lyophilization of the aqueous phase gave the hydrochloride of 1′-ethoxycarbonyloxyethyl 6-(D-α-aminopnenylacetamido)penicillante (94 g), m.p. 171°– 176°C/ (decomp.) $[\alpha]_D^{20}$ +161.5 (C = 1, CHCl$_3$); +171.8 (C = 1, 50% isopropanol) (Found: C 50.06, H 5.82, O 22.26, N 8.35, S 6.56, Cl 7.19 %. Calculated for C$_{21}$H$_{28}$N$_3$O$_7$scl: C 50.24, H 5.68, N 8.37, O 22.31, S 6.39, Cl 7.06 %.)

The product showed strong IR absorption at 1780 – 1750 cm$^{-1}$ due to the β-lactam and ester carbonyls, and was found to inhibit the growth of Staph. Aureus Oxford at a concentration of 0.13 μg/ml.

EXAMPLE 16

1′-Ethoxycarbonyloxyethyl 6-(D-α-aminophenylacetamide) penicillanate.

a. To a suspension of the hydrochloride of α-aminophenylacetyl chloride (2.6 g, 0.0125 mole) stirred in dry chloroform (50 ml) under dry nitrogen sodium bicarbonate (1.1 g, 0.0125 mole) and the hydrochloride of 1′-ethoxycarbonyloxyethyl 6-aminopenicillanate (3.3 g, 0.01 mole) was added. After stirring for 90 minutes the mixture was filtered and isopropanol (15 ml) was added to the filtrate. Evaporation in vacuo at room temperature gave an oily residue which on dilution with petrol ether precipitated the hydrochloride of 1′-ethoxycarbonyloxyethyl 6-(D-α-aminophenylacetamido)penicillanate (1.5 g). The product was purified by precipitation from acetone - petrolether.

The identity of the product was ascertained by comparison of its IR spectrum with that of the product from Example 15.

b. Sodium N-(1-methoxycarbonyl-propen-2-yl)-α-aminophenylacetate (2.5 g, 0.0092 mole) and N-methylmorpholine (0.05 ml) in dry ethyl acetate (40 ml) were stirred and treated at −15°C with isobutyl chloroformate (1.4 g, 0.01 mole). After 6 min 1′-ethoxycarbonyloxyethyl 6-aminopenicillanate (0.01 mole) in ethyl acetate (20 ml) was added dropwise while stirring was continued and the temperature was maintained at −15°C. 10 min after the addition was complete the cooling bath was removed and stirring was continued for 45 min. The reaction mixture was washed with water, 0.5 mole sodium bicarbonate and water again, dried and concentrated in vacuo to an oily residue which was treated with tetrahydrofurane (20 ml) and water (20 ml). The mixture was acidified to pH 2.5 by addition of 2 N hydrochloric acid. After 30 min most of the tetrahydrofurane was removed in vacuo and the acidic aqueous phase was washed with ethyl acetate and evaporated to give the hydrochloride of 1′-ethoxycarbonyloxyethyl 6-(D-α-aminophenylacetamido)penicillanate (0.35 g) as an amorphous solid, identified as the product obtained above by means of its IR spectrum.

The solution of 1′-ethoxycarbonyloxyethyl 6-aminopenicillanate used was obtained by neutralization of an aqueous solution of its hydrochloride and extraction with ethyl acetate.

EXAMPLE 17

Ethoxycarbonyloxymethyl 6-(D-α-aminophenylacetamido) penicillanate.

A stirred suspension of sodium 6-(D-α-azidophenylacetamido) penicillanate (12.1 g, 0.03 mole) in dry dimethylformamide (30 ml) was treated with chloromethylethyl carbonate (4.2 g, 0.03 mole) in dry dimethylformamide (15 ml) in the ice-bath. After 45 min the cooling bath was removed and stirring was continued over night. The dark reaction mixture was poured into twice its volume of saturated sodium bicarbonate solution and the solid phase found was removed by filtration and washed with water and ether. The combined filtrates were extracted with ether. The ether extracts were washed with water, dried and evaporated in vacuo at room temperature to give ethoxycarbonyloxymethyl 6-(D-α-aminophenylacetamido)-penicillanate, (4.7 g) as a brownish oil. The product showed strong absorption bands in IR at 2120 cm⁻¹ and 1780 – 50 cm⁻¹ attributable to the azido group and the β-lactam and ester carbonyls respectively.

The azido ester (2.6 g) was dissolved in 60 % ethanol (50 ml) and hydrogenated for 30 min at 60 p.s.i. over a prehydrogenated Raney-nickel catalyst. The catalyst was removed by filtration and washed with ethanol. The filtrate was diluted with water and extracted with ethyl acetate. The combined organic exstracts were washed with water and then extracted with water by addition of dilute hydrochloric acid until the pH reached 2.5. The aqueous phase was separated and lyophilized to give the crystalline hydrochloride of 1'-ethoxycarbonyloxymethyl 6-(D-α-aminophenylacetamido)penicillanate (0.7 g). The product showed strong IR absorption at 1760 cm⁻¹ and inhibited the growth of *Staph.Aureus* Oxford at 0.05 μg/ml.

EXAMPLE 18

Propoxycarbonyloxymethyl 6-(D-α-aminophenylacetamido) penicillanate

According to the procedure of Example 17 propoxycarbonyloxymethyl 6-(D-α-azidophenylacetamido)-penicillanate (5.2 g) was obtained from sodium 6-(D-α-azidophenylacetamido)penicillanate (12.1 g, 0.03 mole) and chloromethyl n-propyl carbonate (4.6 g, 0.03 mole). It exhibited strong IR-absorption at 2120 cm⁻¹ and 1780 – 1740 cm⁻¹ showing the presence of azido group and of β-lactam and ester carbonyls respectively.

On hydrogenation over Raney-nickel the azido ester (2.9 g) gave propoxycarbonyloxymethyl 6-(D-α-aminophenylacetamido)penicillanate isolated as its hydrochloride (1.0 g). It showed strong β-lactam and ester absorption bands in IR at 1775 cm⁻¹, and inhibited the growth of *Staph. Aureus* Oxford at a concentration of 0.05 μg/ml.

EXAMPLE 19

Isopropoxycarbonyloxymethyl 6-(D-α-aminophenylacetamido)penicillanate.

In the manner described in Example 17 isopropoxycarbonyloxymethyl 6-(D-α-azidophenylacetamido)-penicillanate (7.2 g) was obtained from sodium 6-(D-α-azidophenylacetamido)penicillanate (9.9 g, 0.025 mole) and chloromethyl isopropyl carbonate (3.8 g, 0.025 mole). Its IR spectrum contained strong absorption bands at 2110 cm⁻¹ (azido group) and 1780 – 1740 cm⁻¹ (β-lactam and ester carbonyls).

Hydrogenation over Raney-nickel converted the azido ester (4.4 g) into isopropoxycarbonyloxymethyl 6-(D-α-aminophenylacetamido)penicillanate isolated as its hydrochloride (1.3 g). It showed strong absorption in IR at 1760 cm⁻¹ characteristic for β-lactam and ester carbonyls and inhibited the growth of *Staph. Aureus* Oxford at a concentration of 0.05 μg/ml.

EXAMPLE 20

Butoxycarbonyloxymethyl 6-(D-α-aminophenylacetamido) penicillanate.

According to the procedure of Example 17 butoxycarbonyloxymethyl 6-(D-α-azidophenylacetamido)-penicillanate (6.0 g) was prepared from sodium 6-(D-α-azidophenylacetamido)penicillanate (9.9 g, 0.025 mole) and chloromethyl-n-butyl carbonate (4.2 g, 0.025 mole). The compound showed strong IR absorption at 2120 cm⁻¹ (azido group) and 1780 – 1750 cm⁻¹ (β-lactam and ester carbonyls).

The azido ester (2.9 g) was hydrogenated over Raney-nickel to give butoxycarbonyloxymethyl 6-(D-α-aminophenylacetamido) penicillanate isolated as its hydrochloride (1.0 g). It showed strong IR absorption at 1780 – 1770 cm⁻¹ (β-lactam and ester carbonyls) and inhibited the growth of *Staph. Aureus* Oxford at a concentration of 0.05 μg/ml.

EXAMPLE 21

Ethylcarbamatemethylester of 6-(D-α-azidophenylacetamido)-penicillanic acid.

To an agitated and icecooled dispersion of the sodium salt of 6-(D-α-azidophenylacetamido)-penicillanic acid (98 %, 7.2 g, 0.018 mole) in dry dimethylformamide (18 ml) N-chloromethyl ethyluretan (2.1 g, 0.018 mole) dissolved in dimethylformamide (10 ml) was added. After 40 minutes the stirring was continued over night without cooling.

The reaction mixture was poured into cold sodium bicarbonate solution (400 ml) and extracted twice with ether. The combined ether phases were washed with water and sodium chloride solution and dried. Evaporisation of the ether extract gave the ethylcarbamatemethylester of 6-(D-α-azidophenylacetamido)-penicillanic acid (2.6 g).

After reprecipitation of the product from methylene chloride/petroleum ether 2.3 g was obtained having a purity of 57.7 %.

EXAMPLE 22

1'-acetoxy-ethyl 6-(D-α-amino-m-fluorophenylacetamido) penicillanate.

Hydrochloride of 1'-acetoxyethyl 6-aminopenicillanate (3.4 g, 0.01 mole) in dry dimethylformamide (50 ml) was stirred in the ice-bath and treated with N,N-dimethylaniline (2,4 g, 0.02 mole) followed by a solution of α-azido-m-fluorophenylacetyl chloride (2.1 g, 0.01 mole) in dry ether (5 ml). After stirring for 1 hour water (100 ml) was added and the mixture was adjusted to pH 6.5 and extracted 3 times with ethyl acetate. The combined organic extracts were washed with water and brine, dried and evaporated in vacuo to give 1'-acetoxyethyl 6-(D-α-azido-m-fluorophenylacetamido)penicillanate (1.5 g) as an oily residue. This product showed strong IR absorption at 2110 and 1780 – 1750 cm⁻¹ indicating the presence of the azido group and β-lactam and ester carbonyls.

The azido ester (0.7 g) was dissolved in 60 % ethanol (7 ml) and added to prehydrogenated Raney nickel catalyst (0.7 g) in 80 % ethanol (5 ml) and hydrogenated for 30 min at ambient conditions. The catalyst was removed by filtration and washed with ethanol. The combined filtrates were concentrated in vacuo at 35°C to an oily residue which was dissolved in ethyl acetate. Water (20 ml) was added and the pH was adjusted to 1.6 by addition of 2 N hydrochloric acid to the stirred mixture. The aqueous phase was separated and evaporated in vacuo at 35°C to give the hydrochloride of 1'-acetoxyethyl 6-(D-α-amino-m-fluorophenylacetamido)penicillanate (0.4 g) as a crystalline residue.

The product was found to inhibit the growth of *Staph.Aureus* Oxford at a concentration of 0.25 μg/ml and to contain in its IR spectrum a strong β-lactam absorption at 1760 cm$^{-1}$.

EXAMPLE 23

1'-Ethyloxycarbonyloxyethyl 6-(D-α-amino-m-fluorophenylacetamido)penicillanate.

To sodium 6-(D-α-azido-m-fluorophenylacetamido)-penicillanate (4.2 g, 0.01 mole) and sodium bicarbonate (5.1 g, 0.06 mole) in 70 % dioxane (15 ml) α-chloro-diethylcarbonate (4.6 g, 0.03 mole) was added and the mixture was stirred for 2 days at room temperature. The reaction mixture was filtered. the residue washed with dioxane and the combined filtrates were evaporated to dryness in vacuo. The residue was dissolved in a mixture of benzene (40 ml) and saturated aqueous sodium bicarbonate (20 ml). The organic phase was separated, washed with brine, dried and evaporated to give 1'-ethyloxycarbonyloxyethyl 6-(D-α-azido-m-fluorophenylacetamido)penicillinate (1.0 g).

The product showed strong IR absorption at 2100 and 1750 cm$^{-1}$ corresponding to the azido group and the β-lactam and ester moieties, respectively.

It was dissolved in ethylacetate (10 ml) and added to palladium on carbon (5%) hydrogenation catalyst (0.5 g), prehydrogenated in ethylacetate (5 ml) and hydrogenated for 2 hours under ambient conditions. The catalyst was filtered off and washed with ethylacetate. Water (10 ml) was added to the combined filtrates and pH was adjusted to 2.2 by addition of 2 N hydrochloric acid to the stirred mixture. The aqueous phase was separated, washed with ether and lyophilized to give the hydrochloride of 1'-ethyloxcarbonyloxyethyl 6-(D-α-amino-m-fluorophenylacetamido)penicillanate (0.2 g) as white crystalline residue.

The product was found to contain in its IR spectrum a strong absorption at 1780 cm$^{-1}$ corresponding to a β-lactam ring. It inhibited the growth of *Staph. Aureus* Oxford at a concentration of 0.13 μg/mole.

EXAMPLE 24

1'-Acetoxyethyl 6-(D-α-amino-p-fluorophenylacetamido)penicillanate.

Using the procedure described in Example 23 1'-acetoxyethyl 6 (D-α-azido-p-fluorophenylacetamido)-penicillanate (2.2 g) was prepared from sodium 6-(D-α-azido-p-fluorophenylacetamido) penicillanate (4.2 g, 0.01 mole), α-chloroethyl acetate (3.7 g, 0.03 mole) and sodium bicarbonate (5 g, 0.06 mole). The IR spectrum of the product showed strong absorptions at 2110 cm$^{-1}$ (azido group) and 1775 – 1750 cm$^{-1}$ (β-lactam and ester carbonyls).

The azido ester was hydrogenated according to the procedure described in Example 22 over Raney-nickel catalyst to give the hydrochloride of 1'-acetoxyethyl 6-(D-α-amino-p-fluorophenylacetamido)penicillanate (1.5 g) as slightly yellow crystals. The product showed in its IR spectrum a strong β-lactam and ester absorption at 1765 cm$^{-1}$ and was found to inhibit the growth of *Staph. Aureus* Oxford at a concentration of 0.25 μg/ml.

EXAMPLE 25

1'-Ethyloxycarbonyloxyethyl 6-(D-α-amino-p-fluorophenylacetamido)penicillanate.

To sodium 6-(D-α-azido-p-fluorophenylacetamido)-penicillanate (4.2 g, 0.01 mole) and sodium bicarbonate (5.1 g, 0.06 mole) in 70 % dioxane (15 ml) α-chlorodiethylcarbonate (4,6 g, 0.03 mole) was added and the mixture was stirred for two days at room temperature. The reaction mixture was filtered; the residue washed with dioxane and the combined filtrates were evaporated to dryness in vacuo. The residue was dissolved in a mixture of benzene (40 ml) and saturated aqueous sodium bicarbonate (20 ml). The organic phase was separated, washed with brine, dried and evaporated in vacuo to give 1'-ethyloxycarbonyloxyethyl 6-(D-α-azido-p-fluorophenylacetamido)penicillanate (1.9 g).

The product showed strong IR absorption at 2110 and 1750 cm$^{-1}$ corresponding to the azido group and the β-lactam and ester moieties, respectively. It was dissolved in ethyl acetate (10 ml) and added to prehydrogenated palladium (5 %) as carbon catalyst (0.5 g) in ethyl acetate (5 ml) and hydrogenated for 2 hours under ambient conditions. The catalyst was removed by filtration and washed with ethyl acetate. Water (10 ml) was added to the combined filtrates and pH was adjusted to 2.2 by addition of 2 N hydrochloric acid to the stirred mixture. The aqueous phase was separated, washed with ether and evaporated to dryness in vacuo to give the hydrochloride of 1'-ethyloxycarbonyloxyethyl 6-(D-α-amino-p-fluorophenylacetamido)-penicillanate (0.2 g) as white crystals.

The product was found to contain a strong β-lactam absorption in its IR spectrum at 1760 cm$^{-1}$ and to inhibit the growth of *Staph.Aureus* Oxford at a concentration of 0.25 μg/ml.

EXAMPLE 26

1'-Acetoxyetyl 6-(α-amino-p-chlorophenylacetamido)penicillanate.

Potassium α-azido-p-chlorobenzylpenicillinate (0.55 g, 0.00138 mole) was dissolved in 70 % dioxane (3 ml), treated with sodium bicarbonate (0.63 g, 0.0075 mole) followed by α-chloroethyl acetate (0.45 g, 0.0037 mole) while stirring at room temperature. After two days the reaction mixture was diluted with water and extracted with ethyl acetate repeatedly. The combined extracts were washed with brine, dried and evaporated to give 1'-acetoxyethyl 6-(α-azido-p-chlorophenylacetamido)penicillanate (0.42 g) as a yellow oil.

The product showed strong IR absorption at 2110 and 1770 – 1750 cm$^{-1}$ corresponding to the azido group and the β-lactam and ester moieties, respectively. It was dissolved in 70 % ethanol (7 ml) and hydrogenated for 30 min at 60 p.s.i. over a prehydrogenated Raney-nickel catalyst. The catalyst was filtered off and washed with ethanol. The combined filtrates were diluted with water and extracted with ethyl acetate. Water was added to the organic phase and the pH of the mixture was adjusted to pH 2.2 by addition of dilute hydrochloric acid. Lyophilization of the aqueous phase gave 1'-acetoxyethyl 6-(α-amino-p-chlorophenylacetamido) penicillanate hydrochloride (0.23 g) as a crystalline residue.

The product was found to contain a strong β-lactam absorption in its IR spectrum at 1760 – 1740 cm$^{-1}$ and to inhibit the growth of *Staph. Aureus* Oxford at a concentration of 0.63 μg/ml.

EXAMPLE 27

1'-Acetoxyethyl 6-(D-α-amino-p-hydroxyphenylacetamido)penicillanate.

Sodium (−) N-(1-methoxycarbonylpropen-2-yl)-α-amino-p-hydroxyphenyl acetate (2.9 g, 0.01 mole) in dry ethyl acetate (40 ml) was stirred and treated at −15° to −20°C with N-methylmorpholine (a few drops) followed by isobutylchloroformate (1.4 g, 0.01 mole). After 5 min a solution of 1'-acetoxyethyl 6-aminopenicillanate (3 g, 0.01 mole) in ethyl acetate (20 ml) chilled to − 15°C was rapidly added. After stirring for 60 min without external cooling the reaction mixture was washed with water, 0.5 M potassium bicarbonate, and water, dried and evaporated in vacuo at room temperature to dryness. The residue was dissolved in a 1:1 mixture of tetrahydrofurane and water (50 ml), stirred and kept for 30 min at pH 2.5 by addition of 2 M hydrochloric acid. The tetrahydrofurane was evaporated in vacuo and the remaining aqueous phase was washed with ethyl acetate, diluted with isopropanol and evaporated in vacuo at room temperature to give the hydrochloride of 1'acetoxyethyl 6-(D-α-amino-p-hydroxyphenylacetamido)penicillanate (2.3 g) as white crystals. The product showed in IR strong absorption bands at 1760 cm$^{-1}$ attributable to the β-lactam and ester carbonyls. It was found to inhibit the growth of *Staph.Aureus* Oxford at a concentration of 0.25 μg/ml.

The solution of 1'-acetoxyethyl 6-(D-α-aminophenylacetamido) penicillanate used was prepared by neutralization of an aqueous solution of its hydrochloride and extraction with ethyl acetate.

EXAMPLE 28

1'-Ethoxycarbonyloxyethyl 6-(D-α-amino-p-hydroxyphenylacetamido)penicillanate.

According to the procedure of Example 27 1'-ethoxycarbonyloxyethyl 6-(D-α-amino-p-hydroxyphenylacetamido)penicillanate isolated as its hydrochloride (1.4 g) was prepared from sodium (−) N-(1-methoxycarbonylpropen-2-yl)-α-amino-p-hydroxyphenyl acetate (2.9 g, 0.01 mole) and 1'-ethoxycarbonyloxyethyl 6-aminopenicillanate (0.01 mole).

The product contained in its IR spectrum strong absorption at 1760 cm$^{-1}$, showing the presence of β-lactam and ester carbonyls. It was found to inhibit the growth of *Staph.Aureus* Oxford at 0.25 μg/ml.

EXAMPLE 29

1'-Acetoxyethyl 6-(α-amino-3-furylacetamido)penicillanate.

Sodium N-(1-methoxycarbonylpropen-2-yl)-α-amino-3-furyl acetate (2.5 g, 0.0095 mole) and N-methylmorpholine (0.05 ml in dry ethyl acetate (40 ml) were stirred and treated at −15°C with isobutyl chloroformiate (1.4 g, 0.01 mole). After 5 min 1'-acetoxyethyl 6-aminopenicillanate in ethyl acetate (20 ml) was added dropwise while stirring was continued and the temperature was mainteined at −15°C. 10 min after the addition was complete the cooling bath was removed and stirring was continued for 45 min. The reaction mixture was washed with water, 0.5 mole sodium bicarbonate and water again, dried and concentrated in vacuo to an oily residue which was treated with tetrahydrofurane (20 ml) and water (20 ml) and kept at pH 2.5 for 30 min by addition of dilute hydrochloric acid. Most of the tetrahydrofurane was evaporated in vacuo and the aqueous phase was washed with ethyl acetate and lyophilized to give the hydrochloride of 1'-acetoxyethyl 6-(α-amino-3-furylacetamido)penicillanate (1.9 g) as a white glassy mass.

The product was found to inhibit the growth of *Staph. Aureus* Oxford at a concentration of 0.63 μg/ml and to contain in its IR spectrum a strong absorption at 1760 cm$^{-1}$ attributable to the β-lactam ring and the ester groups.

The solution of 1'-acetoxyethyl 6-aminopenicillanate was obtained by neutralization and extraction with ethyl acetate of an aqueous solution of its hydrochloride. The sodium N-(1-methoxycarbonylpropen-2-yl)-α-amino-3-furyl acetate was prepared by reaction of sodium α-amino-3-furyl acetate and methyl acetoacetate in refluxing toluene.

EXAMPLE 30

1'-Ethoxycarbonyloxyethyl 6-(α-amino-3-thienylacetamido)penicillanate.

In the manner described in Example 29 the hydrochloride of 1'-ethoxycarbonyloxyethyl 6-(α-amino-3-thienylacetamido)penicillanate was prepared from 1'-ethoxycarbonyloxyethyl 6-aminopenicillanate and sodium N-(1-methoxy-carbonylpropen-2-yl)-α-amino-3-thienyl acetate. The product was found to contain a strong absorption at 1760 cm$^{-1}$ in its IR spectrum, showing the presence of β-lactam and ester moieties.

EXAMPLE 31

1'-Acetoxyethyl 6-(α-amino-3-thienylacetamido)penicillanate.

The hydrochloride of 1'-acetoxyethyl 6-(α-amino-3-thienylacetamido)penicillanate (1.2 g) was obtained according to the procedure of Example 29 from sodium N-(1-methoxycarbonylpropen-2-yl)-α-amino-3-thienyl acetate (2.8 g, 0.01 mole) and 1'-acetoxyethyl 6-aminopenicillanate (0.01 mole).

The product showed in its IR spectrum strong β-lactam and ester absorption at 1760 cm$^{-1.}$ The sodium N-(1-methoxycarbonylpropen-2-yl)-α-amino-3-thienyl acetate was obtained by reaction of methylacetoacetate and sodium α-amino-3-thienyl acetate in refluxing toluene.

EXAMPLE 32

Oral absorption in humans of 1'-acetoxyethyl and 1'-ethoxycarbonyloxyethyl 6-(D-α-aminophenylacetamido)penicillanate.

The oral absorption of 1'-ethoxycarbonyloxyethyl 6-(D-α-aminophenylacetamino)penicillanate (I) and of 1'-acetoxyethyl 6-(D-α-aminophenylacetamido)penicillanate (II) was studied in a cross-over experiment in 9 healthy male volunteers using 6-(D-α-aminophenylacetamido)penicillanic acid (ampicillin) as a reference. The compounds were administered in tablets with the following composition:

|   | I | II |
|---|---|---|
| Penicillin ester | 359 mg | 338 mg |
| Corn starch | 101 mg | 102 mg |
| Magnesium stearate | 10 mg | 10 mg |

The amounts of the esters correspond to 250 mg of free ampicillin. The reference compound was given in a commercially available tablet (Doktacillin 0.25 g) containing 250 mg of free ampicillin. The tablets were taken on an empty stomach. Blood samples were drawn at preset intervals and analyzed for their contents of ampicillin using a microbiological essay. The following mean serum levels (in $\mu$g/ml) with standard error of the mean were found:

| Com- pound | Time (hour) | | | | | | | |
|---|---|---|---|---|---|---|---|---|
|  | 0.5 | 1 | 1.5 | 2 | 3 | 4 | 6 | 8 |
| I | 5.99 | 4.79 | 3.47 | 2.51 | 1.14 | 0.71 | 0.20 | 0.069 |
|  | ±0.90 | ±0.35 | ±0.32 | ±0.16 | ±0.13 | ±0.10 | ±0.026 | ±0.011 |
| II | 7.48 | 5.38 | 3.88 | 2.80 | 1.17 | 0.68 | 0.19 | 0.065 |
|  | ±0.86 | ±0.38 | ±0.33 | ±0.38 | ±0.18 | ±0.11 | ±0.035 | ±0.016 |
| Ampi- cillin | 0.48 | 1.49 | 2.30 | 2.28 | 1.66 | 1.52 | 0.35 | 0.12 |
|  | ±0.17 | ±0.29 | ±0.32 | ±0.31 | ±0.25 | ±0.25 | ±0.062 | ±0.026 |

The mean cumulative urinary excretions after 8 hours in percentage of the dose given were:

| I | 53.4 ± 2.5 % |
|---|---|
| II | 53.7 ± 4.9 % |
| Ampicillin | 34.5 ± 2.8 % |

EXAMPLE 33

Hydrolysis of aminopenicillin esters into the corresponding aminopenicillins in buffer and in presence of human serum.

The hydrolysis of the esters of the aminopenicillins prepared according to the invention were determined in buffer solution with and without human serum being present. The esters were incubated for 30 min at 37°C at a concentration of 10 $\mu$g/ml in Sorensen's phosphate buffer (pH 7.4) and in another experiment in the same buffer containing 10 % human serum. The test solutions were extracted with ethyl acetate to remove unhydrolyzed ester and were analyzed microbiologically for their contents of aminopenicillin. Blank values were obtained by dissolving the esters in phosphate buffer at the same concentration and immediately perform the extraction. The values in the table are corrected for the blank values.

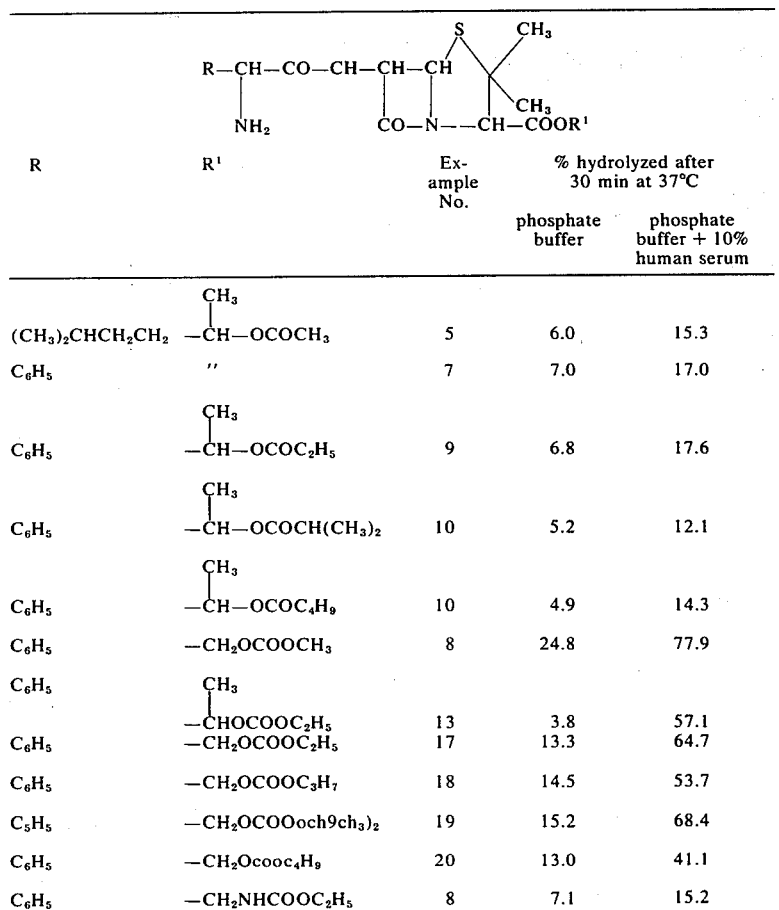

| R | R¹ | Example No. | % hydrolyzed after 30 min at 37°C | |
|---|---|---|---|---|
|  |  |  | phosphate buffer | phosphate buffer + 10% human serum |
| (CH₃)₂CHCH₂CH₂ | —CH(CH₃)—OCOCH₃ | 5 | 6.0 | 15.3 |
| C₆H₅ | " | 7 | 7.0 | 17.0 |
| C₆H₅ | —CH(CH₃)—OCOC₂H₅ | 9 | 6.8 | 17.6 |
| C₆H₅ | —CH(CH₃)—OCOCH(CH₃)₂ | 10 | 5.2 | 12.1 |
| C₆H₅ | —CH(CH₃)—OCOC₄H₉ | 10 | 4.9 | 14.3 |
| C₆H₅ | —CH₂OCOOCH₃ | 8 | 24.8 | 77.9 |
| C₆H₅ | —CH(CH₃)OCOOC₂H₅ | 13 | 3.8 | 57.1 |
| C₆H₅ | —CH₂OCOOC₂H₅ | 17 | 13.3 | 64.7 |
| C₆H₅ | —CH₂OCOOC₃H₇ | 18 | 14.5 | 53.7 |
| C₅H₅ | —CH₂OCOOch9ch₃)₂ | 19 | 15.2 | 68.4 |
| C₆H₅ | —CH₂Ocooc₄H₉ | 20 | 13.0 | 41.1 |
| C₆H₅ | —CH₂NHCOOC₂H₅ | 8 | 7.1 | 15.2 |

-continued $$R-CH-CO-CH-CH-CH \begin{array}{c} S \\ | \\ | \\ NH_2 \end{array} \begin{array}{c} CH_3 \\ | \\ CH_3 \\ CO-N---CH-COOR^1 \end{array}$$

| R | R¹ | Example No. | % hydrolyzed after 30 min at 37°C | |
|---|---|---|---|---|
| | | | phosphate buffer | phosphate buffer + 10% human serum |
| m-F—C₆H₄ | —CH(CH₃)—OCOCH₃ | 22 | 3.1 | 16.4 |
| m-F—C₆H₄ | —CH(CH₃)—OCOOC₂H₅ | 23 | 2.6 | 37.7 |
| p-F—C₆H₄ | —CH(CH₃)—OCOCH₃ | 24 | 9 | 14.3 |
| p-F—C₆H₄ | —CH(CH₃)—OCOOC₂H₅ | 25 | 1.4 | 20.2 |
| p-Cl—C₆H₄ | —CH(CH₃)—OCOCH₃ | 26 | 10.8 | 15.6 |
| p-HO—C₆H₄ | —CH(CH₃)—OCOCH₃ | 27 | 2.5 | 6.8 |
| p-HO—C₆H₄ | —CH(CH₃)—OCOOC₂H₅ | 28 | 5.0 | 33.1 |
| furyl | —CH(CH₃)—OCOCH₃ | 29 | 3.5 | 12.4 |
| thienyl | —CH(CH₃)—OCOCH₃ | 30 | 6.7 | 8.0 |
| " | —CH(CH₃)—OCOOC₂H₅ | 31 | 7.0 | 35.2 |

EXAMPLE 34

Pharmaceutical Formulations.

For preparation of tablets the following compositions were made:

a) 1'-Acetoxyethyl 6-(D-α-aminophenylacetamido)
   penicillanate hydrochloride    338 mg
   Starch    100 mg
   Magnesium stearate    10 mg
b) 1'-Ethoxycarbonyloxyethyl 6-(D-α-aminophenyl-
   acetamido)penicillanate hydrochloride    359 mg
   Starch    100 mg
   Magnesium stearate    10 mg
c) Ethoxycarbonyloxymethyl 6-(D-α-aminophenyl-
   acetamido)penicillanate hydrochloride    350 mg
   Calcium carbonate    100 mg
   Magnesium stearate    10 mg
d) 1'-Ethoxycarbonyloxymethyl 6-(D-α-aminophenyl-
   acetamido)penicillanate hydrochloride    359 mg -continued Lactose    100 mg
   Magnesium stearate    10 mg
e) 1'-Ethoxycarbonyloxymethyl 6-(D-α-amino-m-
   fluorophenylacetamido)penicillanate hydrochloride    370 mg
   Microcrystalline cellulose (Avicel)    100 mg
   Magnesium stearate    10 mg
f) 1'-Acetoxyethyl 6-(D-α-aminophenylacetamido)
   penicillanate hydrochloride    338 mg
   Calcium carbonate    100 mg
   Lactose    100 mg
   Magnesium stearate    10 mg For filling in capsules the following formulations were made:

g) 1'-acetoxyethyl 6-(D-α-aminophenylacetamido)
   penicillanate hydrochloride    350 mg
   Magnesium stearate    5 mg
h) 1'-Ethoxycarbonyloxyethyl 6-(D-α-aminophenyl-
   acetamide)penicillanate hydrochloride    350 mg
   Lactose    40 mg
   Magnesium stearate    5 mg For oral suspensions the following formulations were prepared:

i) 1'-Acetoxyethyl 6-(D-α-aminophenylacetamido)
   penicillanate hydrochloride    34 mg
   Aluminium monostearate    50 mg
   Tween - 80    1.2 mg
   peanut oil    ad 1000 mg
j) 1'-Ethoxycarbonyloxyethyl 6-(D-α-aminophenyl
   acetamide)penicillanate hydrochloride    36 g

| | | |
|---|---|---|
| sodium benzoate | 0.48 | g |
| sodium chloride | 0.75 | g |
| flavouring agents | 4.7 | g |
| Aerosil | 0.3 | g |
| Antifoam | 0.0375 | g |
| alkali salts of polysaccharide sulphates | 4.0 | g |
| sodium saccharinate | 0.4 | g |
| sorbitol | ad 100 | g |

What is claimed is:

1. A pharmaceutical preparation which comprises, as an active ingredient, an anti-bacterially effective amount of at least one compound of the structural formula

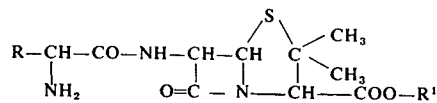

or a pharmaceutically acceptable acid addition salt thereof, in which formula R is the radical

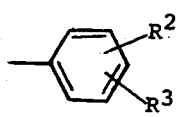

wherein $R^2$ is selected from the group consisting of hydrogen and hydroxy and $R^3$ is selected from the group consisting of hydrogen and halogen such as chlorine and fluorine, and wherein $R^1$ is selected from the group consisting of

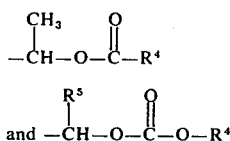

in which formulas $R^4$ is selected from the group consisting of alkyl groups containing from 1 to 4 carbon atoms; and $R^5$ is selected from the group consisting of H, and -$CH_3$, and a pharmaceutically acceptable carrier.

2. A pharmaceutical preparation as defined in claim 1 wherein $R^1$ is

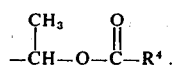

3. A pharmaceutical preparation according to claim 2, wherein R is selected from the group consisting of phenyl and p-hydroxyphenyl and wherein $R^4$ is as defined in claim 2.

4. A pharmaceutical preparation as defined in claim 1 wherein $R^1$ is

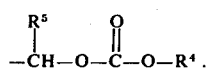

5. A pharmaceutical preparation according to claim 4, wherein R is selected from the group consisting of

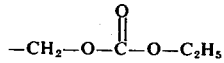

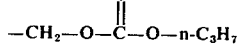

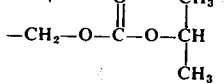

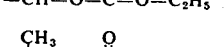

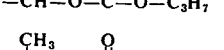

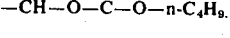

6. A pharmaceutical preparation according to claim 4, wherein R is selected from the group consisting of phenyl and p-hydroxyphenyl.

7. A pharmaceutical preparation according to claim 1, wherein the active ingredient has the structural formula

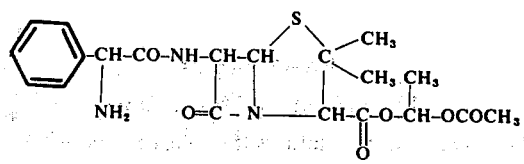

or a pharmaceutically acceptable acid addition salt thereof.

8. A pharmaceutical preparation according to claim 1, wherein the active ingredient has the structural formula

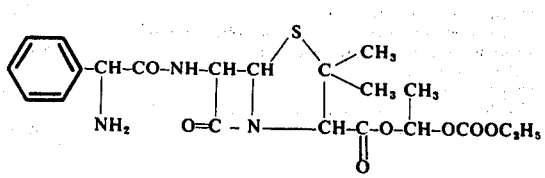

or a pharmaceutically acceptable acid addition salt thereof.

9. A pharmaceutical preparation according to claim 1, wherein the active ingredient has the structural formula

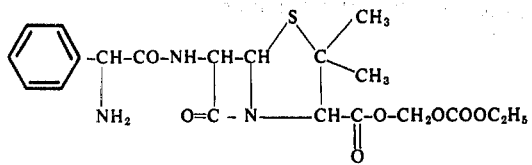

or a pharmaceutically acceptable acid addition salt thereof.

10. A pharmaceutical preparation according to claim 1, wherein the active ingredient has the structural formula

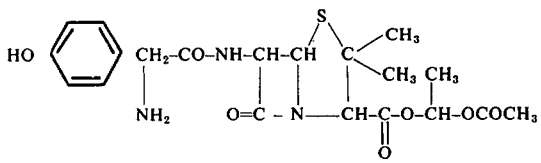

or a pharmaceutically acceptable acid addition salt thereof.

11. A pharmaceutical preparation according to claim 1, wherein the active ingredient has the structural formula

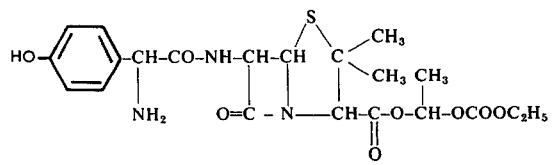

or a pharmaceutically acceptable acid addition salt thereof.

12. A pharmaceutical preparation according to claim 1, wherein the active ingredient has the structural formula

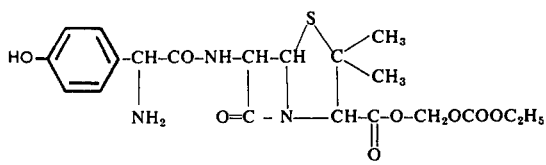

or a pharmaceutically acceptable acid addition salt thereof.

13. A pharmaceutical preparation according to claim 1, wherein the active ingredient has the structural formula

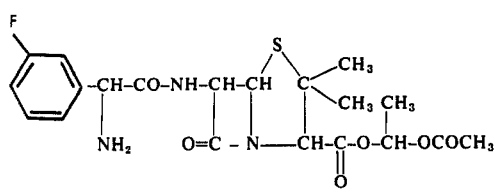

or a pharmaceutically acceptable acid addition salt thereof.

14. A pharmaceutical preparation according to claim 1, wherein the active ingredient has the structural formula

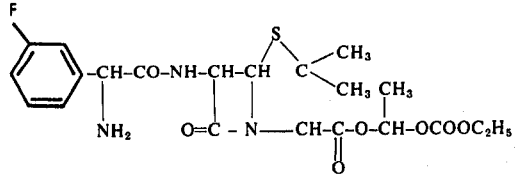

or a pharmaceutically acceptable acid addition salt thereof.

15. A pharmaceutical preparation according to claim 1, wherein the active ingredient has the structural formula

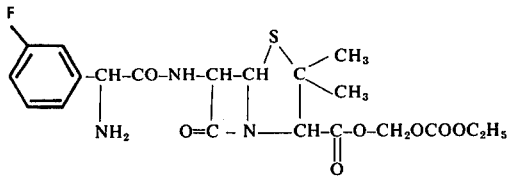

or a pharmaceutically acceptable acid addition salt thereof.

16. A pharmaceutical preparation according to claim 1, wherein the active ingredient has the structural formula

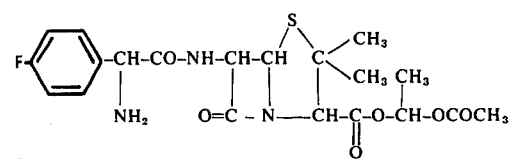

or a pharmaceutically acceptable acid addition salt thereof.

17. A pharmaceutical preparation according to claim 1, wherein the active ingredient has the structural formula

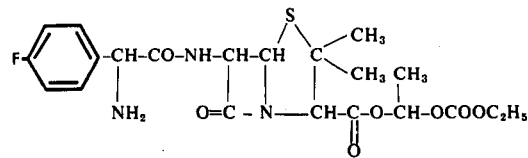

or a pharmaceutically acceptable acid addition salt thereof.

18. A pharmaceutical preparation according to claim 1, wherein the active ingredient has the structural formula

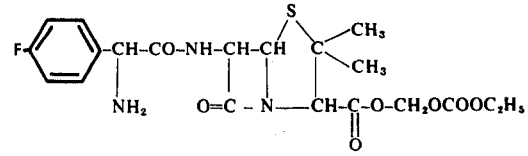

or a pharmaceutically acceptable acid addition salt thereof.

19. A method for the treatment of diseases caused by bacterial organisms, which comprises administering to a human host, suffering from such disease, an anti-bacterially effective amount of the preparation as set forth in claim 1.

* * * * *

UNITED STATES PATENT AND TRADEMARK OFFICE
CERTIFICATE OF CORRECTION

PATENT NO. : 3,939,270
DATED : February 17, 1976
INVENTOR(S) : Bertil Ake Ekstrom and Herndt Olof Harald Sjoberg It is certified that error appears in the above-identified patent and that said Letters Patent are hereby corrected as shown below:

In the Abstract

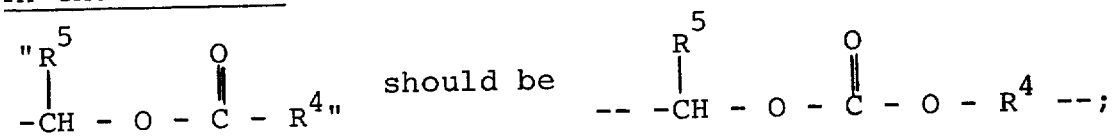

Line 1 under the fourth formula

"-Ch$_2$NHCOO-R$^4$" should be -- -CH$_2$NHCOO-R$^4$ --;

In the Specification

Col. 2, line 23, "α-aminobezylpenicillin" should be -- α-aminobenzylpenicillin --;

In the Patent

Col. 2, line 67, "pharmaceutical" should be --pharmaceutically;
Col. 3, line 1, "disceases" should be --diseases--;
Col. 4, In the Table, first compound under "Name", "-heptylphenicillanate" should be -- -heptylpenicillinate--;

Col. 5-6, In the Table, first compound under "Name", "cillinate should be --cillanate--;

Col. 5-6, In the Table, seventh compound under "Name", "ethoxycqrbonylaminomethyl" should be --ethoxycarbonylaminomethyl--;

Col. 5-6, In the Table, eleventh compound under "Name", "1'-ethoxycqrbonyloxy-ethyl" should be --1'-ethoxycarbonyloxy-ethyl--;

Col. 7-8, In the Table, first compound under "Name", "penicillante" should be --penicillanate--;

UNITED STATES PATENT AND TRADEMARK OFFICE
CERTIFICATE OF CORRECTION

PATENT NO. : 3,939,270
DATED : February 17, 1976
INVENTOR(S) : Bertil Ake Ekstrom and Herndt Olof Harald Sjoberg It is certified that error appears in the above-identified patent and that said Letters Patent are hereby corrected as shown below:

Col. 8, Formula (IV), "-CH" should be -- -CH with N below --;
                      N Col. 9, line 48, "Characteristica" should be --characteristics--;

Col. 9, line 62, "tripehnylmethyl" should be --triphenylmethyl--;

Col. 9, line 64, "acetic" should be --aceto--;

Col. 10, line 10, "chrystallisation" should be --crystallization--;

Col. 10, line 30, "chrystalline" should be --crystalline--;

Col. 10, line 33, "Chrystalline" should be --crystalline;

Col. 11, line 27, "cloride" should be --chloride--;

Col. 13, line 45, "-aminopenicillanate" should be -- -aminopenicillinate--;

Col. 14, line 5, ""benzylpenicillanate" should be --benzylpenicillinate--;

Col. 14, line 32, "aminopenicillanate" should be --aminopenicillinate--;

Col. 14, line 33, "benzylpenicillanate" should be --benzylpenicillinate--;

UNITED STATES PATENT AND TRADEMARK OFFICE
CERTIFICATE OF CORRECTION

PATENT NO. : 3,939,270  
DATED : February 17, 1976  
INVENTOR(S) : Bertil Ake Ekstrom and Herndt Olof Harald Sjoberg It is certified that error appears in the above-identified patent and that said Letters Patent are hereby corrected as shown below:

Col. 15, line 10, "dimethylormamide" should be --dimethylformamide--;

Col. 15, line 34, "caralyst" should be --catalyst--;

Col. 6, line 3, "-164°c,1" should be -- -164°C,/--;

Col. 16, line 16, "aminopenicillanate" should be --aminopenicillinate--;

Col. 17, line 1, "termination" should be --determination--;

Col. 17, line 7, "("°C)" should be --(37°C)--;

Col. 18, line 48, "-ethoxycarbonyloxi" should be --ethoxycarbonyloxy--;

Col. 19, line 15, "isopropanole" should be --isopropanol--;

Col. 19, line 24, "E.coliat" should be -- E. coli at--;

Col. 19, line 59, "lante" should be --lanate--;

Col. 19, line 62, "$C_{21}H_{28}N_3O_7scl$" should be --$C_{21}H_{28}N_3O_7SCl$--;

Col. 20, line 4, "-aminophenylacetamide" should be -- -aminophenylacetamido--;

Col. 21, line 9, "exstracts" should be --extracts--;

UNITED STATES PATENT AND TRADEMARK OFFICE
CERTIFICATE OF CORRECTION

PAGE 4 of 4

PATENT NO. : 3,939,270
DATED : February 17, 1976
INVENTOR(S) : Bertil Ake Ekstrom and Herndt Olof Harald Sjoberg It is certified that error appears in the above-identified patent and that said Letters Patent are hereby corrected as shown below:

Col. 23, line 15, change the period after "filtered" to a comma;
Col. 23, line 22, "penicillinate" should be --penicillanate--;
Col. 25, line 21, "tetrahydrofurane" should be --tetrahydrofuran--;
Col. 25, line 23, "tetrahydrofurane" should be --tetrahydrofuran--;
Col. 26, line 6, "tetrahydrofurane" should be --tetrahydrofuran--;
Col. 26, line 8, "tetrahydrofurane" should be --tetrahydrofuran--;
Col. 28, tenth compound in Table,-"-CH$_2$OCOOoch9ch3)$_2$" should be -- -CH$_2$OCOOCH(CH$_3$)$_2$--;

Col. 28, eleventh compound in Table, - "-CH$_2$Ocooc$_4$H$_9$" should be -- -CH$_2$OCOOC$_4$H$_9$--;

Col. 29, first compound in Table, "Ch$_3$
                                    |
                                   -CH-OCOCH3"    should be

--CH$_3$
  |
 -CH-OCOCH$_3$--;

Col. 33, line 20, "-OCOCH$_3$" should be -- -O$\overset{O}{\overset{\|}{C}}$OCH$_3$--;

Col. 34, line 10,

" 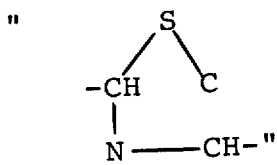    should be   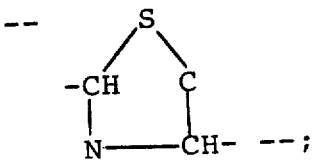 ;

Signed and Sealed this

Second Day of November 1976

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 3,939,270
DATED : February 17, 1976
INVENTOR(S) : Bertil Ake Ekstrom and Berndt Olof Harald Sjoberg It is certified that error appears in the above-identified patent and that said Letters Patent are hereby corrected as shown below:

Col. 31, line 66, "R" should be -- $R^1$ --.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*